United States Patent [19]

Kunstle et al.

[11] 4,129,596
[45] Dec. 12, 1978

[54] PROCESS FOR THE CONTINUOUS PREPARATION OF ACETOACETAMIDES

[75] Inventors: Gerhard Kunstle, Raitenhaslach; Hellmuth Spes, Burghausen; Herbert Siegl, Haiming, all of Fed. Rep. of Germany

[73] Assignee: Wacker-Chemie GmbH, Munich, Fed. Rep. of Germany

[21] Appl. No.: 840,709

[22] Filed: Oct. 11, 1977

[30] Foreign Application Priority Data

Oct. 21, 1976 [DE] Fed. Rep. of Germany ....... 2647499

[51] Int. Cl.$^2$ ............................................. C07C 102/00
[52] U.S. Cl. ................................................. 260/561 K
[58] Field of Search ................................... 260/561 K

[56] References Cited

U.S. PATENT DOCUMENTS

| 3,065,268 | 11/1962 | Mathey et al. | 260/561 K |
| 3,778,474 | 12/1973 | Stocker | 260/561 K |

FOREIGN PATENT DOCUMENTS 962734 7/1964 United Kingdom ................ 260/561 K

*Primary Examiner*—Allen B. Curtis
*Attorney, Agent, or Firm*—Allison C. Collard; Thomas M. Galgano

[57] ABSTRACT

Process for the continuous preparation of acetoacetamides of the general formula $$CH_3COCH_2CO-N-R-R',$$

in which R represents alkyl radicals having from 1 - 18 carbon atoms, and R' represents hydrogen atoms and radical R, by reaction of diketene in stoichiometric ratio with amines of the general formula H—N—R—R', in which R and R' have the meaning given above, which consists of carrying out the reaction for a residence time of not more than 15 minutes and at temperatures of at least 60° C under atmospheric pressure.

3 Claims, 1 Drawing Figure

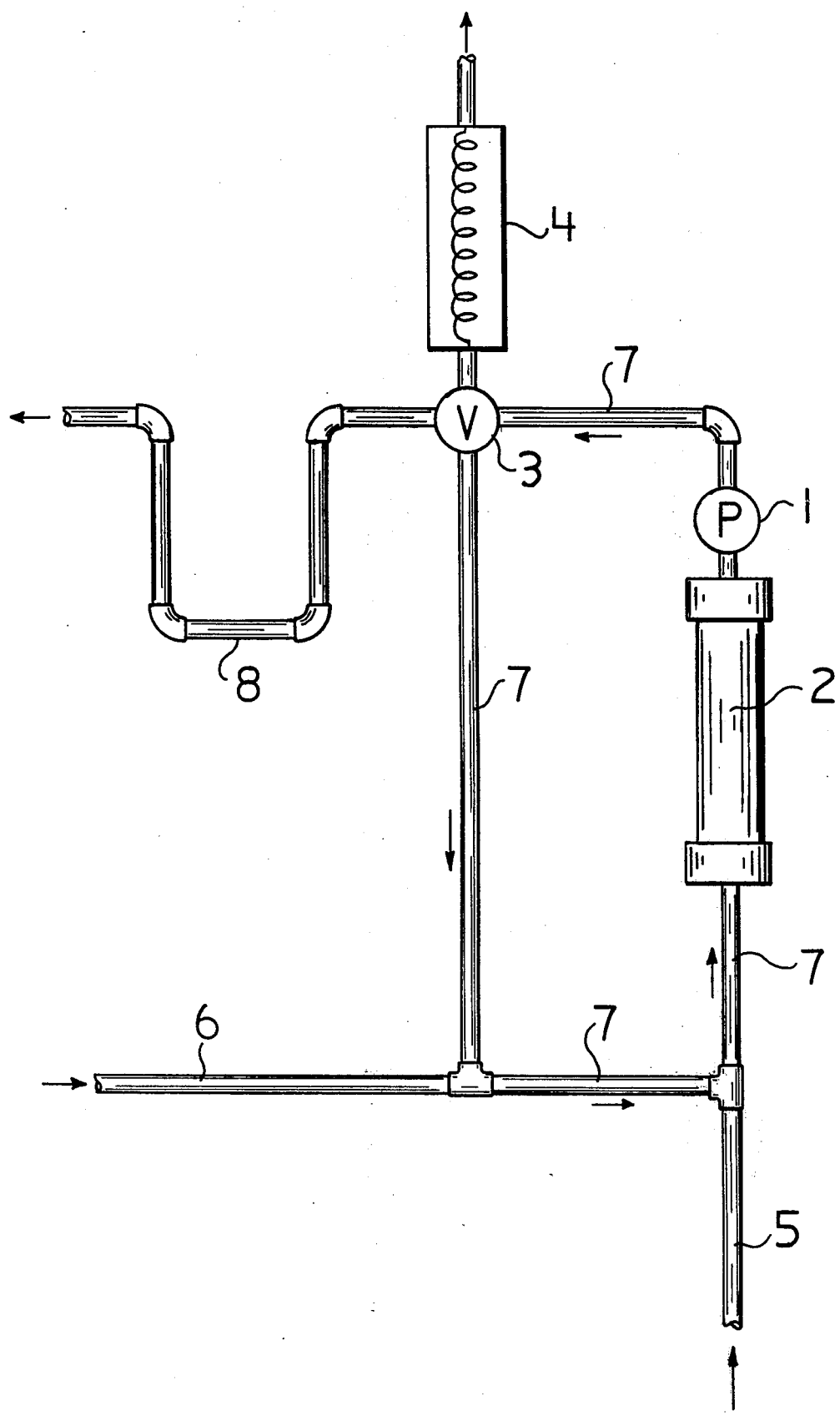

PROCESS FOR THE CONTINUOUS PREPARATION OF ACETOACETAMIDES

The present invention relates to a process for the continuous preparation of acetoacetamides.

It is known to prepare acetoacetamides by reaction of primary or secondary amines with equivalent amounts of diketene in the presence of inert organic solvents or water. However, the separation of the solvent requires not only an additional process step, but is frequently also connected with problems that lead to losses in the yield of the desired product. Attempts to carry out the reaction in the absence of solvents have resulted in an increased formation of undesirable by-products, the removal of which is likewise difficult and only possible with losses in yield.

According to the process described in German Patent Specification No. 1,142,859, the reaction of diketene with primary and secondary aliphatic amines is therefore effected in a medium containing the reaction product, that is, in the presence of the reaction product itself as a reagent, and at reaction temperatures of not more than 80° C., as a result of which the disadvantages of the known processes are avoided and the desired products are obtained in almost quantitative yields and in an industrially useful purity. These details, however, are not illustrated in a verifiable manner by the examples given since, in the examples, operation at reaction temperatures of a maximum of 60° C., either only the yield or only the quality (purity) is given for the product obtained in each case. Moreover, in the examples, there are used as the primary amines only those having at least 6 carbon atoms, whereas methylamine, which is known to be especially reactive, is mentioned, but is not illustrated by any procedural example.

Swiss Patent Specifications Nos. 421,932 and 523,223 confirm that the reaction of diketene and aliphatic amines having lower alkyl radicals can be controlled only with difficulty even with secondary amines. This reaction with diethylamine and dimethylamine is carried out by means of a complicated and expensive electrochemical potential measurement in the presence of an excess of amines and an inert solvent, such as an alkyl acetate or the reaction product itself.

It is the object of the present invention to provide a process for the preparation of acetoacetamides by the reaction of diketene with aliphatic amines, by which both primary and secondary amines are to be understood, which may be carried out continuously, in a simple manner, without the concomitant use of a solvent or diluent, or without the use of an industrially complicated electrochemical potential measurement.

It is a further object of the invention to provide a process by which the desired reaction products, in a verifiable manner, in high yield and in high technical purity are obtained.

The process according to the invention for the continuous preparation of acetoacetamides of the general formula $$CH_3COCH_2CO-N-R-R'$$

in which R represents alkyl radicals having from 1 to 18 carbon atoms, and R' represents hydrogen atoms or radicals R, by the reaction of diketene with amines of the general formula $$H-N-R-R'$$

in which R and R' have the meaning given above, in stoichiometric ratio, comprises carrying out the reaction for a residence time of not more than 15 minutes and at temperatures of at least 60° C. at atmospheric pressure. Examples of radicals R and R', which may be identical or different, are straight-chain or branched alkyl radicals that contain preferably from 1 to 8, and especially from 1 to 4, carbon atoms. Methyl radicals are especially preferred as radicals R, and hydrogen atoms and methyl radicals are especially preferred as radicals R'.

Examples of primary amines which may be used as starting materials in the process according to the invention are methyl, ethyl, n-propyl, iso-propyl, n-butyl, iso-butyl, amyl, hexyl, heptyl, 1,4-dimethylpentyl, octyl, 2-ethylhexyl, lauryl and tridecyl amines.

Examples of secondary amines are dimethyl, diethyl, di-n-propyl, diisopropyl, N-n-propyl-N-isobutyl, dibutyl, diamyl, dihexyl, diheptyl, dioctyl, di-2-ethylhexyl, dinonyl, didecyl, dilauryl, N-ethyl-N-isopropyl, N-ethyl-N-n-butyl and N-methyl-N-isobutylamines.

Methylamine is especially preferred as the primary amine and dimethylamine is especially preferred as the secondary amine.

In the process according to the invention, the reactants are used in stoichiometric ratio, advantageously in pure form, for example freshly distilled form. Preferably, the process is carried out with an excess of diketene of from 0.1 to 2.0%, especailly from 0.1 to 0.5%, of the theoretical amount, since by this means the selectivity under the given conditions may be increased.

For the process according to the invention, the short residence time in conjunction with the relatively high reaction temperatures is of critical significance. The residence time is in this case determined by the reaction volume and the throughput, that is, it is defined as unit of volume/unit of time. Preferably, the reaction is effected for a residence time of from 2 to 10 minutes, and at temperatures of from 80° C. to 150° C.

In carrying out the process according to the invention, the reactants are advantageously fed to a reaction cycle and at the same time reaction mixture is withdrawn from the cycle in order to prevent disruptive accumulation of concentration and heat during the reaction, which proceeds exothermically.

In the accompanying diagramatic drawing, the invention is illustrated by way of example. A reaction cycle for carrying out the process may consist of a circulation pump 1, a heat exchanger 2 and an equalising vessel 3, in addition to a ventilating pipe including a cooler 4, all of which are connected by means of pipe lines 7, forming the cycle.

According to a preferred embodiment of the process of the invention, diketene is fed continuously through a pipe 6, and the amine is fed continuously through a pipe 5 to the reaction cycle 7. At the same time, the circulating reaction mixture is drawn off, likewise continuously, if necessary with cooling, through a pipe 8. The circulated amount, that is, the amount fed through the cycle, may in this case be 50 to 500 times the amount of the starting materials used depending on the type of amine used as reactant.

Attention is drawn to the fact that, under the conditions of the process according to the invention, the selectivity in relation to the desired acetoacetamides is the higher, the shorter is the residence time and the higher is the reaction temperature. Depending on the reactivity of the amine used, however, the residence times and reactive temperatures, which are inversely proportional to one another, may differ and may vary within the specified range. Optimum settings of residence time and reaction temperature can be ascertained for each amine in a simple manner by preliminary experiments. Moreover, the premature reaction of the excess amine with the reaction product can be avoided by the advantageous use of an excess of diketene within the specified range, a fact which has proved especially successful and particularly when using primary amines.

The high selectivity achieved with the process according to the invention, which leads with a quantitative conversion to the desired reaction products in high yield and with an industrially useful purity, must be considered to be surprising, since normally, when using starting compounds which form numerous by-products due to their considerable reactivity, a decrease in selectivity would be expected on increasing the temperature and reducing the reaction time.

Moreover, the process according to the invention enables a high space/time yield to be achieved with a low expenditure on apparatus, which is particularly important for the economy of the process.

Thus, according to the process of the invention, for example, secondary aliphatic amines having lower alkyl radicals, may be converted into the corresponding acetoacetdialkylamides with practically the same selectivity as, but with considerably lower industrial expenditure, than that achieved according to the previously known processes; and primary aliphatic amines having lower alkyl radicals may be converted in a single operation into the corresponding acetoacetmonoalkylamides having an industrially useful degree of purity of up to 96%.

With particular regard to the preparation of acetoacetomonomethylamide, this means that this compound, obtained according to the process of the invention in a degree of purity of about 96%, may subsequently be converted by simple means, for example by thin-layer distillation with a falling-firm or thin-layer evaporator, into a high-purity product which is consequently unaffected by storage. The fine purification by simple distillation is successful only when a starting material of high-percentage is available for this purpose, since in starting material having a purity of only about 86%, azeotropic mixtures form during distillation, and render further purification additionally difficult.

The acetoacetdialkylamides and acetoacetmonoalkylamides of high purity obtained according to the process of the invention are useful intermediates for the manufacture of dyestuffs or — in the form of their corresponding halogen compounds — for the manufacture of plant protectives on the basis of organic phosphoric acid compounds. In this case, and especially for the plant protection field, the purity of the substances used is important, as impurities from the amide preparation can be removed only with difficulty and with apparatus of a considerably complex nature, and, in addition, they promote the formation of highly toxic by-products which not only impair the desired specific action of the plant protection agents, but, above all, are an extreme threat to the environment, a factor which is gaining increasing importance especially as regards the strict demands made for environmental protection.

In the following, the process according to the invention will be described in full detail, but it should be understood that the examples are given only by way of illustration and not of limitation.

EXAMPLE 1

The apparatus used as shown in the drawing consisted of a supply pump 1, whose efficiency was 200 parts by volume/hour of the reaction mixture under the conditions of the experiment; the apparatus further contains a double tube coil condenser 2 and an equalizing vessel 3, in addition to a ventilation pipe 4 capable of being cooled. One, 2 and 3 are joined together by the pipe system 7. The volume of the cycle available for the reaction was 1.7 parts by volume.

10.2 parts by volume, corresponding to 6.724 parts by weight, of almost 100% methylamine, are fed hourly in liquid form through pipe 5 to a point in the cycle 7 immediately upstream of condenser 2. Pipe 6 enters the cycle 7 at a point between equalizing vessel 3 and condenser 2. By this means, 16.79 parts by volume, corresponding to 18.422 parts by weight, of freshly distilled diketene, having a content of 99%, were introduced hourly. The reaction temperature was maintained at 82° C. 23.18 parts by volume, corresponding to 25.146 parts by weight, of hot reaction product were collected hourly from the siphon 8, which on cooling, hardened completely to form yellow-tinged crystalline needles. The average residence time was 4.4 minutes. The melting point of the reaction product was 50° C. and the content of acetoacetic acid methylamide was 95% by weight. This corresponds to a yield of 95.8% of the theoretical.

Subsequently, the reaction product was distilled at 2 torr using a thin layer evaporator, whereupon a colorless distillate boiling at 104° C. was obtained containing 99.3% of acetoacetic acid methylamide.

Table 1 summarizes the results which were obtained in otherwise the same manner by varying the residence time and reaction temperature, respectively.

Table 1

| Reaction Temperature °C | Residence Time Min. | Yield % of theoretical yield | Acetoacetic acid methylamine Content of the reaction product % by weight |
|---|---|---|---|
| 70 | 10 | 86.6 | 87.4 |
| 60 | 30 | 79.4 | 80.1 |
| 40 | 60 | 63.5 | 66.2 |
| 30 | 60 | 62.0 | 65.4 |
| 20 | 120 | 55.8 | 55.8 |

EXAMPLE 2

The apparatus described in Example 1 was used. However, pipe 5 and pipe 6 entered the cycle 7 at the same point immediately upstream of the condenser 2 and the circulation rate of the reaction mixture was 400 parts by volume/hour. Every hour, 12.32 parts by volume, corresponding to 8.145 parts by weight, of almost 100% dimethylamine in liquid form, and 13.99 parts by volume, corresponding to 15.353 parts by weight, of freshly distilled 99% diketene, were fed in, and 22.66 parts by volume, corresponding to 23,498 parts by weight, of hot reaction product were removed while cooling. The average residence time was therefore 4.5 minutes. The reaction temperature was maintained at 85° C.

The content of acetoacetic acid dimethylamide in the reaction product was 98.7% by weight, which corresponds to a yield of 99.4% of the theoretical. The boiling point of the acetoacetic acid dimethylamide was 100° C. at 5 torr.

EXAMPLES 3 to 9

The apparatus described in Example 1 was used, and the process was carried out as indicated therein. Table 2 lists the experimental conditions and the results which were obtained by the reaction of various amines with diketene.

Table 2

| Example No. | Reaction temperature °C | Mean residence time min. | Amine used Content 99% | Reaction Product Type | Content % by wt. | Yield % of theor. yield | m.p. | b.p./torr |
|---|---|---|---|---|---|---|---|---|
| 3 | 90 | 4 | diethylamine | acetoacetic acid diethylamide | 99.0 | 98.5 | | 114° C/4 |
| 4 | 85 | 6 | 2-ethylhexylamine | acetoacetic acid 2-ethylhexylamide | 96.0 | 98.0 | | 130° C/0.01 |
| 5 | 95 | 6 | di-2-ethylhexyl-amine | acetoacetic acid di-2-ethylhexylamide | 97.0 | 98.5 | | 152° C/0.02 |
| 6 | 80 | 10 | diisopropylamine | acetoacetic acid diisopropylamide | 93.5 | 97.5 | | 74° C/0.03 |
| 7 | 90 | 15 | N-n-propyl-s-butylamine | acetoacetic acid n-propyl-s-butyl-amide | 97.0 | 97.0 | | 86° C/0.01 |
| 8 | 115 | 6 | dodecylamine | acetoacetic acid dodecylamide | 95.5 | 98.0 | 82° | |
| 9 | 95 | 8 | tridecylamine | acetoacetic acid tridecylamide | 96.5 | 98.0 | | 191° C/1.5 |

What is claimed is:

1. A process for the continuous preparation of acetoacetamides of the general formula $$CH_3COCH_2CO-N-R-R',$$

in which R represents alkyl radicals having from 1 to 18 carbon atoms, and R' represents a member of the group consisting of hydrogen atoms and radicals R, by reaction of diketene in stoichiometric ratio with amines of the general formula $$H-N-R-R',$$

in which R and R' have the meaning given above, which consists of carrying out the reaction for a residence time of at the most 15 minutes and at temperatures of at least 60° C. under atmospheric pressure.

2. The process according to claim 1, wherein the reaction is carried out for a residence time of from 2 to 10 minutes and at temperatures of from 80° to 150° C.

3. The process according to claim 1, wherein the reaction is carried out with an excess of diketene of from 0.1 to 2.0% of the theoretical amount.

* * * * *